United States Patent [19]

Berglund

[11] Patent Number: 5,270,056
[45] Date of Patent: Dec. 14, 1993

[54] PARTICLE HAVING A DYED COKE INDICATOR AND A PHARMACEUTICAL COATING FOR PARENTERAL ADMINISTRATION OF THE PHARMACEUTICAL

[75] Inventor: Bengt G. Berglund, Göteborg, Sweden

[73] Assignee: Aktiebolaget Hassle, Molndal, Sweden

[21] Appl. No.: 754,284

[22] Filed: Aug. 30, 1991

Related U.S. Application Data

[63] Continuation of Ser. No. 349,895, May 5, 1989, abandoned, which is a continuation of Ser. No. 922,063, Oct. 20, 1986, abandoned.

[30] Foreign Application Priority Data

Oct. 25, 1985 [SE] Sweden .............................. 8505834

[51] Int. Cl.$^5$ ............................................. A61K 9/14
[52] U.S. Cl. ................................... 424/490; 424/495; 428/403; 514/951
[58] Field of Search ............... 424/471, 468, 440, 490, 424/493, 495; 428/406

[56] References Cited

U.S. PATENT DOCUMENTS

| | | | |
|---|---|---|---|
| 2,738,303 | 3/1956 | Blythe | 424/490 X |
| 2,921,001 | 1/1960 | McDermott | 424/471 X |
| 3,054,724 | 9/1962 | Raff | 424/490 X |
| 3,922,339 | 11/1975 | Shear | 424/490 X |
| 4,248,857 | 7/1981 | Deneale et al. | 424/493 |
| 4,432,966 | 2/1984 | Zeitoun et al. | 424/471 X |
| 4,517,006 | 5/1985 | Drake et al. | 428/406 |
| 4,764,375 | 8/1988 | Paradissis | 424/440 |
| 4,767,789 | 8/1988 | Blank et al. | 424/499 |
| 4,927,640 | 5/1990 | Dahlinder et al. | 424/495 |

FOREIGN PATENT DOCUMENTS

| | | | |
|---|---|---|---|
| 657259 | 3/1938 | Fed. Rep. of Germany | 424/471 |
| 2288513 | 5/1976 | France | 424/471 |
| 8101247 | 8/1982 | Sweden | |
| 0756900 | 9/1956 | United Kingdom | 424/471 |
| 800973 | 9/1958 | United Kingdom | 424/471 |

Primary Examiner—Edward Webman
Attorney, Agent, or Firm—White & Case

[57] ABSTRACT

A particle containing a liquid-soluble active substance for release outside a human or animal body, said particle comprising a core with a coating thereon, said coating comprising a liquid soluble active substance, is characterized in that the core has an appearance differing from the appearance of the coating, and that the appearance of the core is initially concealed by the coating and appears after dissolution of the liquid-soluble active substance, thus indicating that the active substance in said coating has been dissolved. The invention has its foremost application on granules, tablets and similar drug releasing units which make part of a parenteral liquid administration device.

6 Claims, No Drawings

PARTICLE HAVING A DYED COKE INDICATOR AND A PHARMACEUTICAL COATING FOR PARENTERAL ADMINISTRATION OF THE PHARMACEUTICAL

This application is a continuation of application Ser. No. 349,895, filed on May 5, 1989, now abandoned, which is a continuation of application Ser. No. 922,063, filed on Oct. 20, 1986, now abandoned.

The present invention is related to a particle such as a granule, a pellet or a tablet, containing a liquid-soluble active substance for release outside a human or animal body said particle comprising a core with a coating thereon said coating comprising such liquid-soluble active substance. The object of the invention is to provide a visual signal which indicates that the liquid-soluble substance, completely or at a pre-determined part, has been consumed.

The invention has its primary application on granules, tablets and similar drug releasing units which are comprised in a parenteral liquid administration device of the kind shown in Swedish patent application No. 8101247-8, and is useful for administering many different drugs as disclosed in that application, for example quinidine, digoxin, lidocaine, glucagon and other hormones and dexamethasone, cardiac glucosides, steroids, theophylline, isosorbide dinitrate, nitroglycerin; antineoplastic drugs e.g. methotrexate, nitrogen mustard and cyclophosphamide; L-hyoscyamine; protein drugs e.g. insulin; sedatives and anaesthetics such as different barbiturates; analgesics such as morphine; tranquilizers such as chloropromazine; cardiovascular agents not mentioned above e.g. dopamine; other agents like gentamicin sulphate; and agents for prophylactic use against deep vein thrombosis like heparin. Derivatives or salts of compounds mentioned may also be of interest. In this case granules or tablets comprising a drug substance, or another substance suitable for parenteral administration, are placed in a cell through which the liquid of a parenteral liquid administration system is flowing, whereby said substance is dissolved by the liquid administered to the patient. In this connection it may be of great value to be able to observe the consumption of the drug to be able to take adequate measures, such as activation of a further drug dosage or disconnection of the liquid supply when a predetermined amount of the drug has been consumed.

DESCRIPTION OF THE INVENTION

According to the invention the core in the particle mentioned initially has an appearance differing from the appearance of the coating, and the appearance of the core is initially concealed by the coating and appears after the dissolution of the liquid-soluble active substance, thus indicating that the active substance in said coating has been dissolved.

Thus, the coating and the core preferably have colours differing from each other. When the coating contains a drug substance the coating is often white, while the core can be for example blue. The visual difference between the core and the coating can alternatively be achieved for example by different surface structure or different fluorescence properties. It is thus within the scope of the invention that the difference in appearance is detectable only in special light or by means of special apparatus, but a difference in appearance that is detectable with the eye in normal light is preferred.

The core is preferably a core insoluble in the liquid, such as a plastic bead or a glass bead which may be dyed with a desired colour or coated with a dye and a protective layer which prevents dissolution in the case that the dye is soluble in the liquid. Said protective layer may consist of a water-insoluble impermeable polymer. If said protective layer is used, the core may then also be soluble in the liquid The coating can be a coating which contains the liquid-soluble active substance and has an ability to conceal the core, but it is also possible to achieve the concealing property of a coating by means of a layer which is placed inside the layer comprising the liquid soluble substance. Said layer can thereby either by soluble in the liquid or have an ability to change from being opaque to being transparent through influence of the liquid.

The layer which comprises the liquid soluble substance can in a manner known per se be provided with release controlling agents, such as a matrix in which the substance is intermixed, for example a polymer matrix where the polymer is insoluble or soluble in the liquid, or an outer membrane comprising a water-insoluble polymer. If said outer membrane is not dissolved by the liquid it will be made of a transparent material or a material which by the influence of the liquid becomes transparent.

The liquid soluble substance is preferably a substance suitable for parenteral administration which can be dissolved in a liquid suitable for parenteral administration. Thus, the liquid-soluble active substance may be a drug with healing or alleviating effect, a diagnostic, or a nutrient. Substances useful for continuous or intermittent infusion may be utilized. More than one liquid soluble substance may be used in a particle according to the invention. Examples of drugs are antibiotics, cardiovascular agents such as lidocaine and $\beta$-blockers, cytostatics or gastric acid secretion inhibiting agents. The liquid suitable for parenteral administration is usually an aqueous solution such as an isotonic sodium chloride solution or a dextrose solution. Substances which facilitate the dissolution of liquid soluble substance such as polyethyleneglycol as well as other additives may be used.

Particles according to the invention intended to be used in a plurality suitably have the size of 0.5–4 mm.

Preparation of particles according to the invention is suitably done by coating in a fluidized bed, but coating in a coating pan and other techniques, for example coacervation, may be used. A process for preparation of one or more particles according to the invention is a further aspect of the invention.

Use of one or a plurality of particles according to the invention in a device for parenteral liquid administration, the device mentioned initially, is a further aspect of the invention. Thereby naturally the cell in which the body/bodies is placed will be transparent or designed in another way, so that the change of appearance may be observed.

In addition to its use in parenteral liquid administration the invention can be applied in other technical fields, for example in laboratories, whereby the liquid soluble active substance may be a chemical reagent.

The invention is further described by the following example:

Cores 500 g non pareil (sugar-starch beads) fraction 1.18–1.4 were used. These core are white, and therefor the beads were coloured blue with 0.13 g methyleneblue in 408 g 95% ethanol together with 25 g ethylcellulose as an adhesive. An insoluble polymer (25 g ethylcellulose) was then laid on to prevent leakage. The active substance consisting of 500 g lidocaine hydrochloride dissolved in 360 g methylenechlorid/isopropanol (50:50% by weight) was then spray-crystallized on the blue coloured cores which turned white. A release control film (50 g ethylcellulose dissolved in 2100 g methylenechlorid/isopropanol (75:25% by weight) was then laid on the granules. The entire process was carried out in a fluidized bed in a 0.5 kg scale. Release tests carried out showed that the granules changed colour from white to blue at the end of the release.

I claim:

1. A particle for the parenteral administration of a pharmaceutical which is to be dissolved outside the body of an animal and subsequently administered to the animal and for monitoring the course of the administration, said particle having a size of 0.5-4 mm and comprising:

an inactive colored core selected from the group consisting of dyed plastic beads, dyed glass beads and dyed sugar-starch beads wherein the beads are insoluble or are coated with a protective layer that is insoluble; and a coating comprising a liquid-soluble active pharmaceutical substance, having a color different from the color of the core, surrounding and visually concealing the core such that visualization of the core provides a means for monitoring dispersal of the pharmaceutical substance.

2. A particle according to claim 1 wherein the liquid-soluble active substance is dissolved in a parenteral administration liquid.

3. A particle according to claim 2 wherein the particle releases the active substance into a parenteral administration liquid.

4. A particle according to claim 1 wherein the coating comprising the liquid-soluble active substance is provided with an agent which controls the release of the substance to a parenteral administration liquid.

5. A process for preparation of a particle according to claim 1 wherein the core is provided with a coating of liquid-soluble active substance, which coating has an appearance differing from the appearance of the core so that the core is concealed by the liquid-soluble active substance and is exposed after the release of the active substance thus indicating that the active substance has been released.

6. A method for parenterally administering and monitoring the administration of a pharmaceutical which is to be dissolved outside the body of a mammal and subsequently administered to the mammal comprising:

introducing into a parenteral administration liquid a particle having a size of 0.5–4 mm, the particle comprising an inactive colored core selected from the group consisting of dyed plastic beads, dyed glass beads and dyed sugar-starch beads wherein the beads are insoluble or are coated with a protective layer that is insoluble, and a coating containing an active, liquid-soluble pharmaceutical substance with a color different from that of the core, surrounding and visually concealing the core such that visualization of the core occurs when the solvent dissolves a predetermined amount of the liquid-soluble substance, thus providing a means for monitoring dispersal of the pharmaceutical.

* * * * *

UNITED STATES PATENT AND TRADEMARK OFFICE
CERTIFICATE OF CORRECTION

PATENT NO. : 5,270,056
DATED : December 14, 1993
INVENTOR(S) : Bengt G. Berglund It is certified that error appears in the above-indentified patent and that said Letters Patent is hereby corrected as shown below:

On the title page: item [54] and in col. 1, line 2, change "COKE" to "CORE;"

Col. 2, line 14, change "by" to --be--;

Col. 2, line 66, after "Cores," insert --of--; and

Col. 2, line 67, after "1.4," insert --mm--.

Signed and Sealed this

Third Day of February, 1998

Attest:

BRUCE LEHMAN

Attesting Officer

Commissioner of Patents and Trademarks